United States Patent [19]

Barthels

[11] 4,412,546
[45] Nov. 1, 1983

[54] CARDIAC MONITORING APPARATUS

[75] Inventor: Richard N. Barthels, Mesa, Ariz.

[73] Assignee: Medtronic, Inc., Minneapolis, Minn.

[21] Appl. No.: 245,559

[22] Filed: Mar. 19, 1981

Related U.S. Application Data

[63] Continuation of Ser. No. 37,407, May 9, 1979, abandoned.

[51] Int. Cl.³ .............................................. A61B 5/04
[52] U.S. Cl. ................................................ 128/709
[58] Field of Search ............... 128/639, 641, 644, 689, 128/690, 696, 703, 706, 710, 709

[56] References Cited

U.S. PATENT DOCUMENTS

| | | | |
|---|---|---|---|
| 3,058,458 | 10/1962 | Daneman | 128/709 |
| 3,323,514 | 6/1967 | Barrett, Jr. | 128/696 |
| 3,338,234 | 8/1967 | Kleinerman et al. | 128/710 |
| 3,343,528 | 9/1967 | Kirkham | 128/709 |
| 3,534,727 | 10/1970 | Roman | 128/644 |
| 3,858,034 | 12/1974 | Anderson | 128/703 |
| 3,858,574 | 1/1975 | Page | 128/689 |
| 3,911,905 | 10/1975 | Rossel | 128/709 |
| 4,026,278 | 5/1977 | Ricketts et al. | 128/644 |
| 4,040,412 | 4/1977 | Sato | 128/641 |
| 4,120,294 | 10/1978 | Wolfe | 128/690 |

Primary Examiner—William E. Kamm
Attorney, Agent, or Firm—Glenn W. Bowen; John L. Rooney; Joseph F. Breimayer

[57] ABSTRACT

A wristwatch size cardiac monitoring apparatus which is worn on the wrist of one arm which in a first mode use a conductive material housing as one electrode which is held firmly in contact with the wrist of the arm on which it is worn. A finger of the other arm is placed on a receiving electrode of the casing which acts as a second electrode. Together, these two electrodes provide a lead I electrocardiac signal to the electronics within the housing. The monitoring apparatus can operate in a second mode when an external belt and set of sensors is plugged into a jack in the side of the housing. The set of sensors are positioned using the belt on opposite sides of the patient's chest just below the pectoral muscles and in contact with the skin. Additionally, there is described circuitry which is used to operate the rate monitor with either the internal or the external sensors.

7 Claims, 6 Drawing Figures

U.S. Patent  Nov. 1, 1983  Sheet 1 of 3  4,412,546
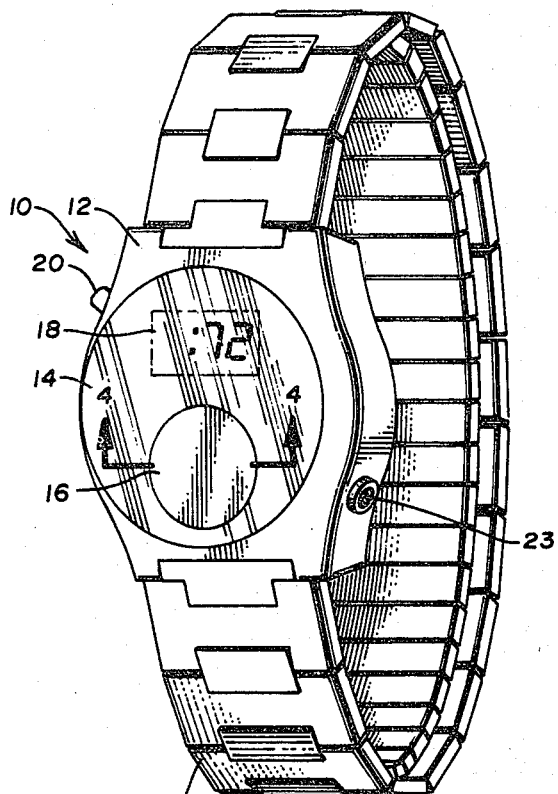
Fig.1
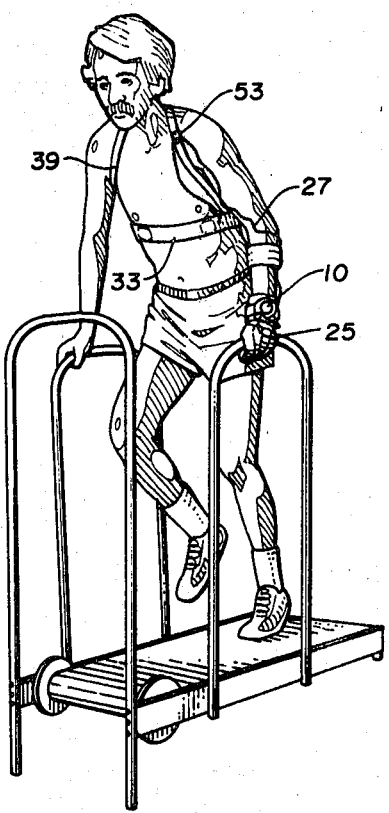
Fig.3
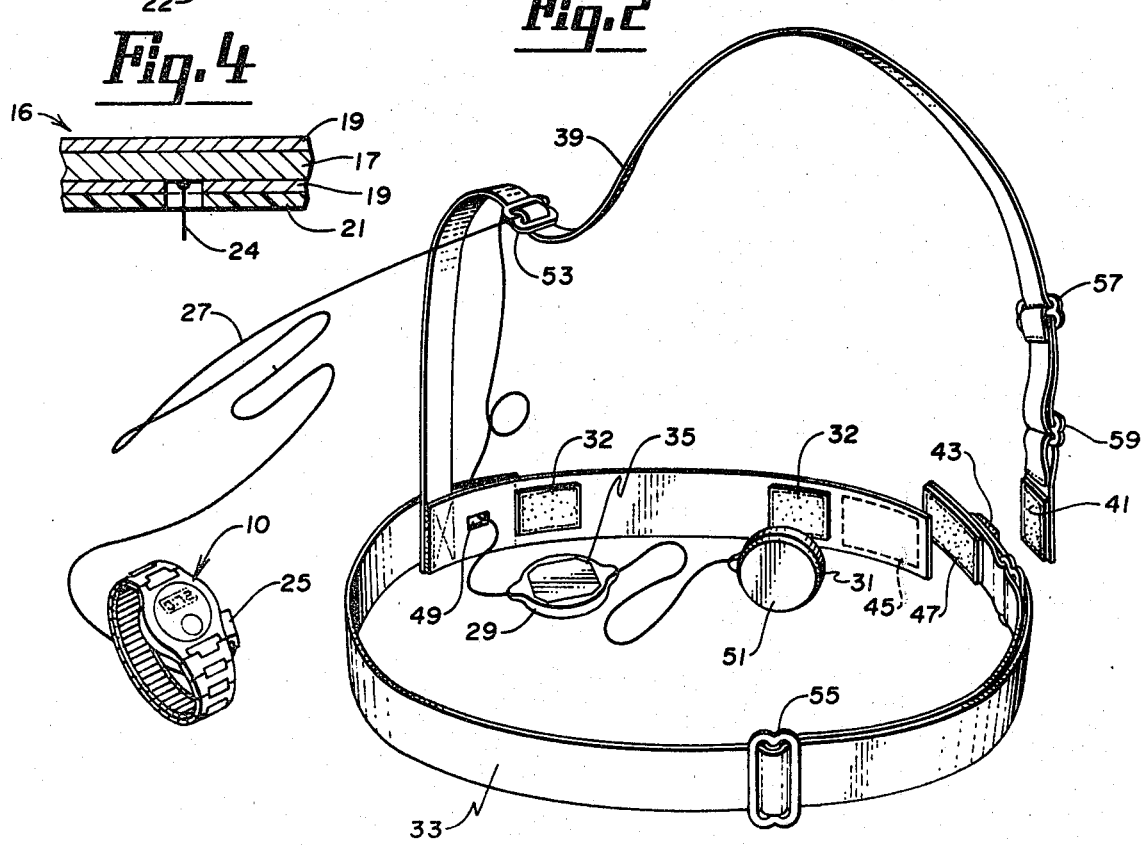
Fig.4
Fig.2

4,412,546

CARDIAC MONITORING APPARATUS

This application is a continuation of application Ser. No. 37,407, filed May 9, 1979, now abandoned.

DESCRIPTION

1. Background of Prior Art

This invention relates to portable cardiac monitoring apparatus, and, more particularly, to such apparatus adapted to be worn on a wrist of a user which in one operating mode utilizes the back of the watch casing to constitute one input electrode and an additional electrode insulated from the casing placed on the front of the watch to constitute a second electrode, whereby a lead I EKG signal can be derived. In a second operating mode, the monitoring apparatus utilizes external sensors attached to a belt which is used to secure the sensors on opposite sides of the user's chest.

This invention is an improvement over the prior art cardiac monitoring apparatus disclosed in pending applications Ser. Nos. 909,229 and 909,230, in the names of Rolf W. Linden and Larry R. Larson, respectively, which applications are assigned to the assignee hereof. Those two applications pertain to the sensors and circuitry for a wrist mounted digital pulse sensor. In the device disclosed in those applications, no provision is made for the utilization of external sensors with the monitoring apparatus. For some users and under certain conditions, the cardiac monitoring apparatus disclosed in those patent applications may not provide adequate sensing of the EKG signal during physical exercise. For those situations, it is necessary to utilize external electrodes maintained in contact with the skin of the chest close to the heart. Either of the above discussed patent applications, nor the prior art discussed in the applications, disclose portable cardiac monitoring apparatus which can be utilized with both self-contained and external sensors.

A wristwatch size cardiac rate monitor is disclosed in the two co-pending applications which are discussed above. In the cardiac rate monitor disclosed in those applications, the signal detected is developed between the limbs of the wearer and is detected by placing the user's finger on top of a layer of dielectric material which covers a metal layer on the face of the wristwatch size cardiac monitoring apparatus while the second electrode is the case of the apparatus itself, which is attached directly to the wrist of one arm. For some users, and under some conditions, it is not possible to detect the electrocardiac signal adequately using the self-contained sensors. For some patients, the self-contained sensors will not detect the electrocardiac signal at all and for may other patients, it is extremely difficult to detect the electrocardiac signal during strenuous exercise. For these persons and conditions, it is necessary to utilize remote sensors held against the rib area with an elastic strap or harness to provide the electrocardiac signal input to the detecting circuitry.

BRIEF SUMMARY OF THE INVENTION

According to one aspect of this invention, there is provided on the portable cardiac rate monitor a means for providing a signal from external sensors to permit the detection of a lead I electrocardiac signal horizontally across the user's chest. The signal from the external sensors in such cases is substituted for the lead I electrocardiac signal developed across the two upper limbs utilizing the case of the monitor and a sensor in physical contact with the other limb. The improvement herein is a receiving or a receptacle means on the case for receiving an electrical signal from external sensors and circuitry for utilizing that signal rather than the signal generated from the self-contained sensors to develop the display of the pulse rate.

BRIEF DESCRIPTION OF THE DRAWINGS

A preferred embodiment of the present invention is hereafter described with specific reference being made to the following figures in which:

FIG. 1 shows a rate monitor in accordance with the present invention;

FIG. 2 is a pictorial view of a pair of remote sensors and their electrical interconnection wiring;

FIG. 3 is a pictorial view of a user wearing the rate monitor and the external sensors in a harness arrangement;

FIG. 4 is a cross section of the self-contained sensor 16 shown in FIG. 1; and

DETAILED DESCRIPTION OF THE INVENTION

Figure 5A:
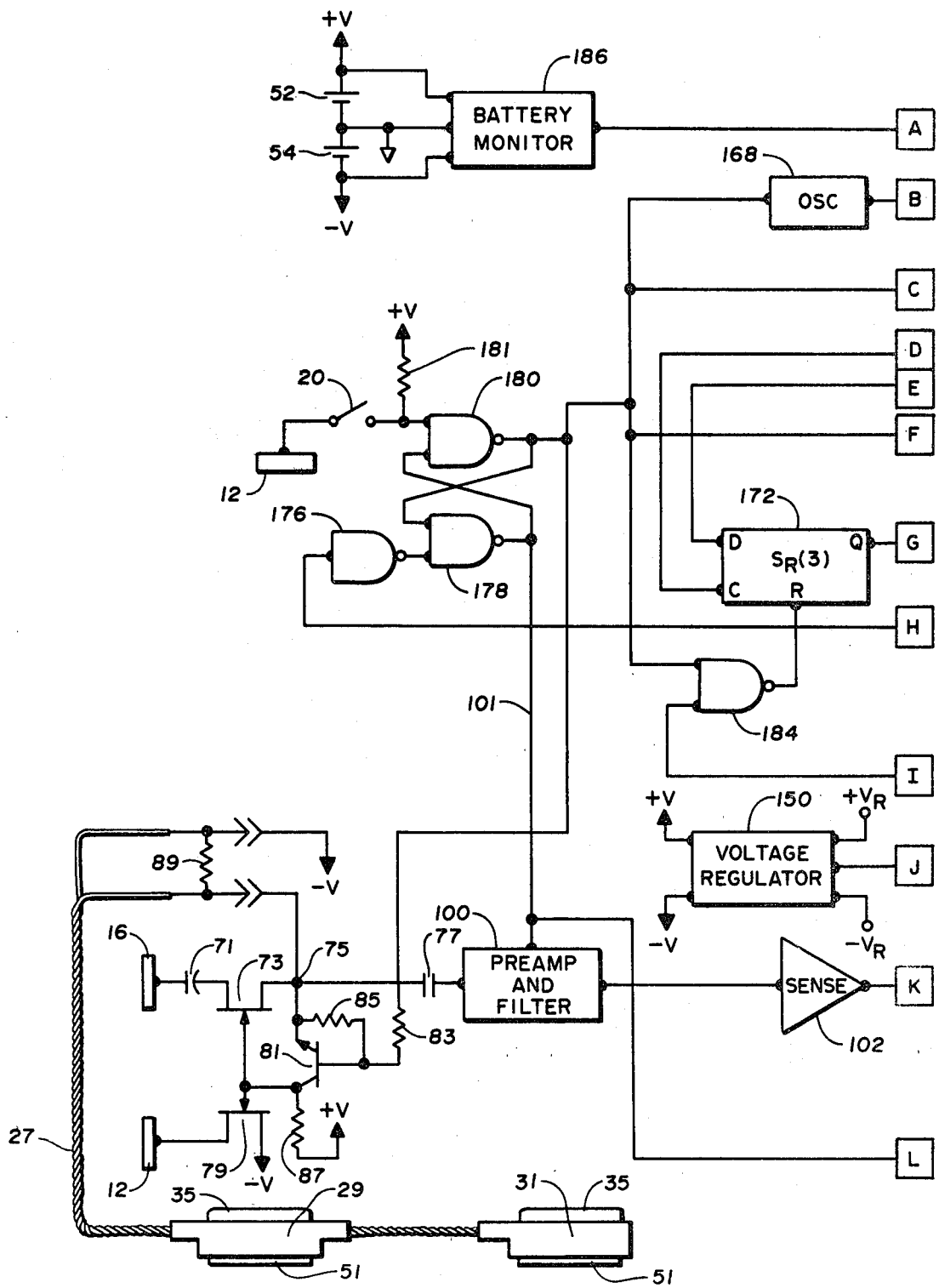
FIGS. 5a and 5b are an electrical schematic diagram showing the electrical circuit used with the rate monitor of this invention.

Referring now to FIG. 1, a wrist rate monitor 10 is shown, and includes a casing 12 of a conductive material such as stainless steel having a face plate 14 which may be of material such as mineral glass that is silk screened with a paint on the rear surface, and inserted therein. Face plate 14 has inserted therein an electrode 16.

Electrode 16, shown in cross section in FIG. 4 is a 0.5 inch diameter of 0.05 inch thick tantalum disc 17 that has an oxide layer 19 on the exposed side which is approximately 3500 Å thick and shown thicker than scale in FIG. 4 for clarity. This electrode is an improvement over the thick film electrode disclosed in the co-pending applications to Rolf Linden and Larry Larson identified above. The dielectric formed by the oxide layer on the tantalum disc is very hard by comparison with the thick film type. It therefore provides a dielectric surface for sensor 16 that will not chip or change characteristics from body oils and salts which may affect thick film types.

The oxide layer 19 on the tantalum disc 16 can most easily be applied to both surfaces during the anodization process. As shown in FIG. 4, the back side of disc 16 has a plastic retainer 21 applied thereto with an aperture therein to permit connection of a lead wire 24 to the surface of the disc 16. Prior to attachment of the wire 24 to the back of disc 16, the oxide layer 19 in the area of the connection must be removed by scraping with a file tip or similar hard abrasive instrument. The lead 24 is then secured, in close electrical contact, to the tantalum disc using a conductive elastomer.

In addition to the sensor on the face plate 14, there is a clear opening for a display 18, such as commercially available liquid crystal displays or light emitting diode displays. Housing 12 also includes an on-off switch 20 which is to be depressed and spring released each time it is desirous to turn on rate monitor 10.

Additionally, rate monitor 10 includes a conventional expansion watchband 22, attached in a manner similar to the way one is attached to a conventional wristwatch. The purpose of watchband 22 is to secure casing 12 firmly in contact with the wrist in order to get an electrical signal provided thereto as one part of a lead I EKG signal when the monitor is operated in its first mode utilizing the self-contained sensor 16. Finally, rate monitor 10 includes a jack or receptacle 23 which may be connected to a corresponding plug 25 connected to a conductor pair 27 and external sensors 29 and 31 shown in FIG. 2.

As is well known in the art, a lead I EKG signal is a signal taken generally horizontally across the heart. This signal is conventionally derived by locking at the difference in signals taken between the two arms of the subject. Conventionally, the signals are derived from the wrist areas of both arms, although they can be derived from any area such as the shoulders or the fingers. When monitor 10 is operated using the self-contained sensor 16, the lead I EKG is taken between the wrist of one arm and a finger of the other arm by casing 12 being held by band 22 in contact with the wrist of one arm and the user placing a finger from the other arm in contact with the self-contained electrodes 16. As indicated above, electrode 16 is a capacitance type electrode which includes a disc 17 of conductive material, such as tantalum, and a thin layer of dielectric material 19 such as tantalum oxide. An electrical connection 24 is provided between the conductive material 17 and the electronic components within housing 12. When the user's finger is applied to the dielectric material of the sensor means 16, a capacitor is formed, with the finger being one plate and the conductive material 17 being the second plate. The voltage at the skin of the finger is transferred through the dielectric to the other plate of the capacitor and from there to the electrical components of the circuit, where the heart rate is determined and displayed on display 18.

Referring now to FIGS. 2 and 3, there is shown a pair of external sensors 29 and 31 and their interconnecting wiring 27 and plug 25. Plug 25 is inserted into receptacle 23 on case 12 of monitor 10 when it is necessary to utilize the external sensors to provide an adequate signal when the patient intends to exercise heavily or if for any reason it is not possible to measure the user's pulse rate using the self-contained sensor 16. The external sensors are held in place over the user's chest utilizing an elastic belt 33. Each of the sensors 29 and 31 has a velcro interlocking strip 35 attached to its reverse face which can be connected to a corresponding interlocking fastener 37, which is located on the inner surface of belt 33. A neck strap 39 is connected at one end to belt 33 and has a fastener 41 at its other end for connection to an interlocking fastener 43 attached to belt 33. The two ends of belt 33 have interconnecting velcro fasteners 45 and 47, which are used to releasably secure the belt about the user's chest. Belt 33 also has a hole 49 through which the twisted pair wire 27 is passed.

The sensors 29 and 31 are made from a relatively flexible epoxy and have a hydrophilic and conductive PVC electrode 51 having approximately a 1.125 inch diameter and 0.030 inch thickness bonded to their front surface. The surface of the electrode 51 is treated with an abrasive such as fine sandpaper to remove the glaze to give it a hydrophilic property. Since electrode 51 is hydrophilic, natural body moisture can supply the body/skin interface rather than using an electrode gel.

As shown in FIG. 4a, the signals from the electrodes 51 of ground reference sensors 29 and signal sensor 31 are connected to the monitor via a matched twisted pair insulated wire cable 27. Both leads extend the full length of the cable between the ground lead sensor 29 and the end of the cable at signal sensor 31 being approximately 9 inches. The electrode 51 of signal sensor 31, the length between sensor 29 and sensor 31 is attached in an ohmic connection to the signal lead of pair 27 while the other or ground lead is attached in an ohmic connection to electrode 51 of sensor 29 although twisted with, but not connected to the signal lead which is connected to signal sensor 29. One wire of the twisted pair 27 is attached to the electrode of sensor 29 while the other wire is attached to the electrode 31.

FIG. 3 shows the sensor belt 33 and the neck strap 39 in place on a user who is wearing the monitor 10 on his left wrist. The twisted pair 27 is connected through a "wire buckle" 53 which acts as a strain relief to minimize the tugging of the twisted pair connections to sensors 29 and 31. The length of belt 33 can be adjusted using sliding buckle 55, and the length of the neck strap 39 can be adjusted using sliding buckle 57 and buckle 59. The belt must fit snugly so that there is no movement between the sensors and the user's skin during a rapid inhaling or exhaling motion. The belt 33 is positioned around the narrowest portion of the rib cage just below the pectoral muscles, as shown in FIG. 3, with the sensors 29 and 31 against the skin at the front of the body.

Figure 5B:
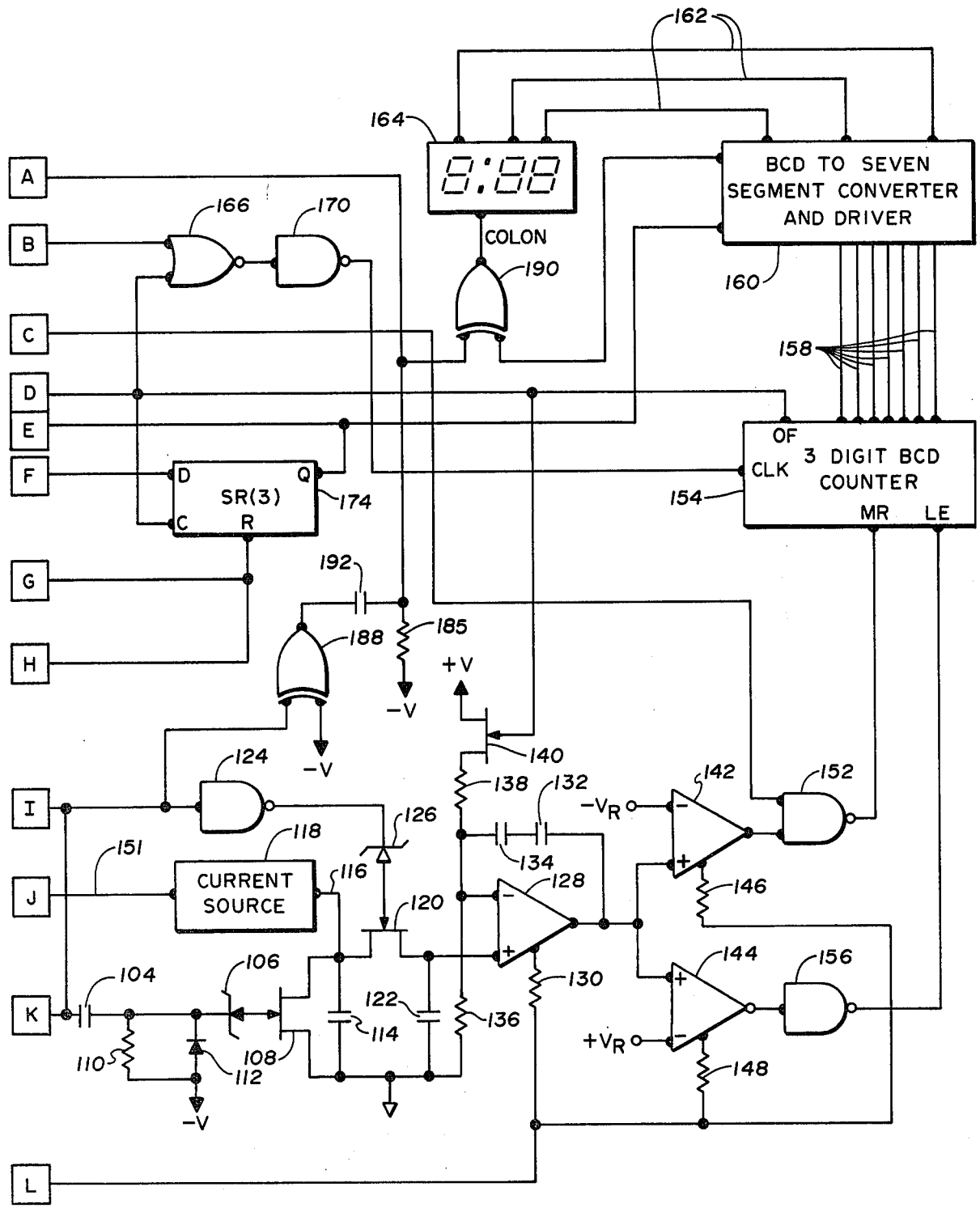

Referring now to FIGS. 5a and 5b, there is shown an electrical schematic diagram of the circuitry used in operating monitor 10. In the following discussion and in FIGS. 5A and 5b, devices 73, 79, 120, and 140 are described and drawn as N channel JFET transistors. The actual devices that accomplish these functions are section of a quad analog CMOS switch. The input signal from finger electrode 16 is applied through capacitor 71 to one terminal of an N channel field effect transistor 73, which has its other main terminal connected to a junction point 75, which is in turn connected through a capacitor 77 to the input of preamp filter circuit 100. The case 12 of monitor 10 is connected to one of the main terminals of a field effect transistor 79, while the other main terminal is connected to the negative supply voltage. When the monitor is operating with the internal sensors 12 and 16 only and the external sensors 29 and 31 are not plugged into monitor 10 using plug 25, the gate of field effect transistor switches 73 and 79, are forward biased by turning those switches on while NPN transistor 81 is off because there is no current path established to permit a current to be driven through the base emitter junction of transistor 81 to turn it on. The emitter of transistor 81 is connected to junction point 75 while the base is connected through a resistor 83 to the output of NAND gate 180, the operation of which will be discussed later. A further resistor 85 is connected between the base and emitter of transistor 81 and a collector resistor 87 is connected between the collector of transistor 81 and the positive voltage supply.

When inputs from the remote electrodes 29 and 31 are selected by inserting plug 25 in receptacle 23 in the case 12 of monitor 10, a current path is established between junction point 75 and the negative supply through resistor 89 and the voltage at junction point 75 is pulled down to approximately the voltage of the negative voltage supply. When the external sensors are initially connected, the voltage at the output of gate 180 is in a low or minus V potential state so that the voltage at the collector of transistor 81, which is applied to the bases of field effect transistors 73 and 79, is at a potential equal to the positive supply and switches 73 and 79 are on. Since switch 79 is on, the case 12 is at minus V potential and enables the start switch 20 to function because it is referenced to the case potential. Closing start switch 20 causes the output of gate 180 to switch to a high potential turning transistor 81 on because the voltage at junction 75 is held at a low level by the path through resistor 89 to the negative supply. When transistor 81 is on its collector is at a low voltage turning off switches 73 and 79 to block signals from the internal electrode 16, which would introduce noise and a motion artifact while the user is exercising, which would cause erratic readings in the displayed heart rate.

The remainder of the circuitry shown in FIGS. 5a and 5b is identical to the circuitry shown in FIG. 5 of the co-pending applications of Rolf Linden and Larry Larson, identified above and fully described in those applications. Accordingly, the operation of those portions of the monitor is only generally described herein.

The signal from either the remote sensors 29 and 31 or the integral sensors 16 is connected through capacitor 77 to the input of preamp and filter 100, which includes conventional preamp filter circuits utilizing operational amplifiers with appropriate biasing and feedback. The biasing circuits may be reverse biased by a negative voltage signal applied to line 101 so that circuit 100 draws virtually no current during the time monitor 10 is not in use.

The output from the preamp and filter circuit 100 is applied to a conventional cardiac signal detecting amplifier 102 as disclosed for example in U.S. Pat. No. 4,059,116. Since amplifier 102 provides a negative-going two msec wide pulse upon detection of an EKG signal.

After an output pulse is delivered from sense amplifier 102 the circuitry of the amplifier rejects any subsequent signals for approximately 300 miliseconds to prevent other waves in the EKG signal which follow the QRS wave from being detected as additional heart beat waves. Thus, the sense amplifier 102 will have a maximum response rate of 200 pulses per minute. The sense amplifier output pulses occur at the same rate as the heart beat rate and thus provide a logic level signal triggered by and synchronized with the heart. When the positive going edge of the sense amp output pulse occurs, field effect transistor 108 is turned off and allows current source 118 to begin to charge capacitor 114 until the next falling edge of a sense amplifier output pulse turns on field effect transistor switch 120, which transfers some of the charge across capacitor 114 to capacitor 122. Field effect transistor 120 stays on for the duration of the two milisecond sense amp pulse width and during that time capacitor 104 charges up through diode 112. When the input pulse goes back positive, switch 120 is turned off and capacitor 104 pulls the gate of switch 108 positive, turning it on and discharging capacitor 114. Following the two milisecond time constant of capacitor 104 and resistor 110, switch 108 turns off and the current source begins charging capacitor 114 again. The voltage will increase in a ramp fashion until the next sense amp pulse arrives, at which time capacitor 122 is again updated. If the time interval between input pulses is constant, the voltage across capacitor 122 will stabilize at the peak value of the ramp across capacitor 114.

The pulse to pulse spacing resulting from sensing a slower heart rate will cause a greater peak voltage on capacitor 114 because the current source 118 will continue to charge the capacitor for a longer time interval before switch 108 resets the capacitor. The resulting voltage across capacitor 122 is inversely proportional to the heart rate and is updated on a beat to beat basis. Capacitor 122 also serves to average out irregularities in the pulse to pulse time interval.

The signal across capacitor 122 is applied as a reference input voltage to the integrator formed from amplifier 128, capacitors 132 and 134, and resistor 136. The integrator is reset and released on two second intervals by switch 140. The slope of the ramp at the output of the integrator is controlled by the voltage level at the input and becomes steeper for greater input voltages across capacitor 122.

The output of the operational amplifier 128 of the integrator is connected to the noninverting inputs of amplifiers 142 and 144 which have their respective inverting imputs connected to reference voltages minus $V_R$ and plus $V_R$ respectively, which are generated by a voltage regulator 150. When the integrator is reset by switch 140, the outputs of both amplifiers 142 and 144 are in a low state, since the reference voltages are more positive than the integrator output. Following reset, the output of the integrator is a positive increasing ramp and first crosses the minus $V_R$ threshhold, causing that comparator 142 to switch to a high output. After a further time interval, the ramp crosses the plus $V_B$ threshhold and switches the other comparator 144 to a high output state. The ramp increases until operational amplifier 128 of the integrator saturates and causes the output to level off until the integrator is reset by switch 140.

The output from amplifier 142 is provided to one input of the two input NAND gate 152. The other input of NAND gate 152 is a signal which is high during normal operation of the circuit, but after automatic shutdown becomes low to thereby disable the passage of any signals through gate 152. The output of gate 152 is applied to the master reset (MR) input of a three-digit binary coded decimal (BCD) counter 154. Whenever the output of gate 152 goes to a logic "0" or low level, counter 154 is enabled to count the pulses applied to the clock (CLK) input thereof.

The output from amplifier 144 is applied through inverter 156 to the latch enable (LE) input of counter 154. A single negative going pulse signal applied to the latch enable input of counter 154 causes signals to appear on the output lines 158 of counter 154, which signals manifest the count of counter 154 at the time the signal was applied through inverter 156 to the latch enable input. The signals on lines 158 continue to appear until another signal is applied to the latch enable input of counter 154. Lines 158 are applied to corresponding inputs of a binary coded decimal (BCD) to seven segment converter and driver circuit 160, which in turn supplies signals on lines 162 to a liquid crystal display 164. In this manner, the count which was latched in counter 154 by the signal through inverter 156 is converted and displayed at display 164. This count is equal to the beat per minute heartbeat rate of the person utilizing rate monitor 10.

Counter 154 continues counting after a signal is applied to the latch enable input thereof, until it reaches a full count. The frequency of the clock providing the clock signals, the clock input of counter 154 and the maximum count of counter 154 are preselected so that counter 154 reaches a full count after a preselected update time, which may be approximately two seconds. For instance, the frequency of the clock signal may be 500 Hz and the maximum count of counter 154 may be 1000. When counter 154 reaches a full count, a signal appears at the overflow (OF) output thereof. This signal is applied to the base of transistor 140 to render it conductive. This causes a high voltage to be applied to the inverting input of operational amplifier 128, which in turn causes the output thereof to go low. When the OF signal is removed, transistor 140 turns off and integrating capacitors 132 and 134 begin charging, thereby raising the voltage at the inverting input of amplifier 128 causing the voltage at its output to begin decreasing in a linear ramp fashion.

During the time when the voltage at the output of operational amplifier 128 is more positive than $-V_R$ volts, the output of operational amplifier 142 is high and thus the output from gate 152 is low. During this period of time, counter 154 remains in the overflow condition because the overflow output is additionally provided to one input of NOR gate 166. The other input of NOR gate 166 has applied thereto the output from oscillator 168 which provides pulses at a frequency of 500 Hz when enabled by a signal on the enable input thereof. When output of NOR gate 166 is provided to inverter 170 to the clock input of counter 154. Whenever counter 154 goes to the overflow state, NOR gate 166 is blocked from passing the oscillator pulses and counter 154 remains in the overflow state until reset by a high signal applied to the master reset input.

As the voltage at the output of integrator amplifier 128 decreases below the $-V_R$ value, the output of amplifier 142 changes states, thereby causing the output of NAND gate 152 to become positive. This low-to-high swing at the output of NAND gate 152 causes counter 154 to be reset to a low count, thereby removing the signal from the overflow output thereof. This, in turn, removes the inhibition at gate 166 and clock pulses are again applied to counter 154. However, counter 154 cannot count upward because of the high signal applied to its reset input. As the voltage at the output of integrator amplifier 128 increases above the $-V_R$ value, the output of amplifier 142 changes state, thereby causing the output of NAND gate 152 to become low. This will remove the reset condition of counter 154, so it begins to count upwards.

As the output of amplifier 128 goes above $+V_R$ volts, the output of amplifier 144 changes states, as does the output at inverter 156 and the latch enable input of counter 154 again causes the signal to be latched to the output lines 158. This continues such that approximately every two seconds, the output lines 158 receive a new reading of the heartbeat.

The overflow output from counter 154 is additionally applied to the clock (C) input of two three-stage shift register circuits 172 and 174. In addition, each of shift registers 172 and 174 have a data (D) input and a reset (R) input and a Q output. Each time a signal is applied to the clock input of one of shift registers 172 and 174, the signal appearing at the data input is stored in the first stage thereof, the signal previously in the first stage is stored in the second stage and the signal previously stored in the second stage is stored in the third stage and appears as the signal at the Q output of the shift register.

The Q output from shift register 174 is coupled to the data (D) input of shift register 172 and additionally coupled to provide voltage to the BCD to seven segment converter and driver circuit 160. Until the Q output of shift register 174 goes high, there can be no display of a signal because no supply voltage is applied to BCD to seven segment converter and driver 160. The Q output from shift register 172 is applied to the reset input of shift register 174 and, in addition, through inverter 176 to one input of two input NAND gate 178. The output of NAND gate 178 is applied to one input to two input NAND gate 180, the output of which is applied back to the other input of NAND gate 178. The other input of NAND gate 180 receives a low, or logic "0", signal each time the switch 20 of rate monitor 10 is momentarily depressed.

NAND gates 178 and 180 connected in the manner described constitute a conventional set-reset latch circuit which becomes set whenever a low signal is applied at the input of gate 180 by closing switch 20 to remove the positive voltage at the input which is connected through resistor 181 to the positive supply. When switch 20 is momentarily closed, the output of gate 180 becomes high and the output of gate 178 low. The low output from gate 178 is fed back to the input of NAND gate 180 to maintain in at a high state. Whenever a low signal is applied from the output of inverter 176, as a result of the Q output of shift register 172 going high, the output of NAND gate 178 is forced high, thereby forcing the output of NAND gate 180 low. This, in turn, maintains the output of NAND gate 178 high.

The output from NAND gate 178 is applied to control the bias of amplifiers 128, 142, and 144. This is done by applying the output from NAND gate 178 through respective resistors 130, 146 and 148. When the output of NAND gate 178 goes low, the amplifiers 128, 142 and 144 are allowed to operate. When the output of NAND gate 178 goes high, the biasing mechanisms within amplifiers 128, 142 and 144 are reverse biased and thus the amplifiers 128, 142 and 144 are shut down and draw negligible current. This is provided in order to save power when the rate monitor is not being used. In addition, the output from NAND gate 178 is coupled to line 101 to reverse bias the operational amplifiers included in preamp and filter circuit 100 in the same manner as just described with respect to amplifiers 128, 142 and 144.

The output from NAND gate 180 is applied as the second input to two input NAND gate 152 and enables NAND gate 152 to operate and pass signals to reset counter 154. At the time of shutdown of the circuit shown in FIGS. 4a and 4b, the output of NAND gate 180 goes low, which causes the output of NAND gate 152 to become high, thereby resetting counter 154.

The output of NAND gate 180 is also applied as the data input of shift register 174 and as one input to NAND gate 184. The other input of NAND gate 184 is the pulse provided at the output of sense amplifier 102. Thus, as long as the circuit is powered up, that is, NAND gate 180 is set and provides a high output, the output from NAND gate 184 will be high each time a pulse is detected, thereby resetting all the stages of shift register 172. In addition, the output of NAND gate 180 is applied to the enable input of oscillator 168 to enable it to provide pulses to counter 154 through gates 166 and 170.

In operation, the above described circuit components prevent a display from happening for six seconds after the switch 20 is depressed and signals begin appearing at the input of amplifier 102. At the time switch 20 is closed, the output of gate 180 goes high, counter 154 begins counting and approximately two seconds later, the first signal appears at the overflow output therefrom.

This shifts the high value then appearing at the data input of shift register 174 into the first stage. It also shifts a low value into the first stage of shift register 172. After two seconds, a second overflow signal appears and shifts high values into both the first and second stages of shift register 174. After the third two second period, all three of the stages of shift register 174 will contain high values and the Q output of shift register 174 becomes a high value. This provides voltage to enable the BCD to seven segment converter and driver circuit 160. This initial six second period is required in order to enable capacitor 122 to stabilize to the voltage to which capacitor 114 is charged and to maintain its value.

If for some reason the user of the device removes his finger from electrode 10 or disconnects the external sensors, heartbeat signals will stop being applied through circuit 100 and detected by amplifier 120. During the period when heartbeats were continually detected, shift register 172 was continually reset by the output from gate 181 and the Q output thereof never achieved a high state. However, with removal of an applied cardiac signal, shift register 172 will now begin shifting high values therethrough and six seconds later the Q output thereof will attain a high state. This high state will be inverted by inverter 176 and reset the latch consisting of NAND gates 178 and 180, thereby causing the output of NAND gate 178 to go high and the output of NAND gate 180 to go low. When the output of NAND gate 178 goes high the bias is removed and amplifiers and the circuit begins shutting down. Also at the time that shift register 172 goes high, shift register 174 is reset and power is removed from the BCD to seven segment driver 160.

Exclusive OR gate 188 and capacitor 192 and resistor 194 connected as shown in FIG. 5 constitute a monostable multivibrator which generates a pulse signal each time a signal is received from sense amplifier 102. This signal controls exclusive OR gate 190 which also receives a back plane output from converter and driver 160. causing the output of XOR gate 190 to invert the back plane signal during the pulse period. Since the back plane output from converter and driver 160 is inverted, the colon display is caused to blink each time a heartbeat is detected. The blinking of the colon indicates to the user that the battery is providing sufficient voltage for proper use.

In the event the battery monitor senses a low voltage, the input to exclusive OR gate 190 from the battery monitor circuit 186 is forced high and thus the output of exclusive OR gate 190 is out of phase with the other input. This in turn maintains the colon in a continuous display state and thus indicates to the user that the battery should be changed.

In the circuit described above, component values for the parts are listed below. Numbered components which are a part of a larger circuit are preceded by the designation P/O.

Capacitor 71: 1.0 microfarads
Transistor 73: P/O MC4066B
Capacitor 77: 0.1 microfarads
Transistor 79: P/O MC4066B
Transistor 81: 2N2484
Resistor 83: 1 Mohms
Resistor 85: 1 Mohms
Resistor 87: 1 Mohms
Capacitor 104: 0.001 microfarads
Diode 106: MZC 5.1A10
Transistor 108: 2N4338
Resistor 110: 2 Mohms
Diode 112: IN914
Capacitor 114: 0.22 microfarads
Transistor 120: P/O MC4066B
Capacitor 122: 0.47 microfarads
Inverter 124: P/O MCC14572
Diode 126: MZC5.1A10
Amplifier 128: P/O ICL8023C
Resistor 130: 20 Mohms
Capacitor 132: 0.22 microfarads
Capacitor 134: 0.22 microfarads
Resistor 136: approximately 250 Kohm (trimmed for accuracy of BPH converter)
Resistor 138: 10 Kohms
Transistor 140: P/O MC4066B
Amplifier 142: P/O ICL8023C
Amplifier 144: P/O ICL8023C
Resistor 146: 1 Mohm
Resistor 148: 1 Mohm
Gate 152: P/O MCC14011B
Counter 154: MCC14553B
Inverter 156: P/O MC14572
Converter and Driver 160: DF411
Display 164: MCL154
NOR gate 166: P/O MCC14572
Gate 170: P/O MCC14572
Shift Register 172: P/O MCC14015B
Shift Register 174: P/O MCC14015B
Inverter 176: P/O MC14572
Gate 178: P/O MCC14011B
Gate 180: P/O MCC14011B
Resistor 181: 3 Mohms
Gate 182: P/O MCC14572
Gate 184: P/O MCC14011B
Resistor 185: 20 Mohm
Gate 188: P/O MCC14070B
Gate 190: P/O MCC14070B
Capacitor 192: 0.033 microfarads
+V: 1.5 volts
GND: 0 volts
−V: −1.5 volts
+$V_R$: +0.3 volts
−$V_R$: −0.9 volts Having described the invention by way of the above examples and general description, the subject matter in which exclusive rights are claimed is defined as follows:

1. In an electrical cardiac monitoring system including signal
processing means, enabling means for enabling said signal processing means, an input circuit path for coupling electrocardiac signals to said signal processing means, switch means coupled so as to change the state of said enabling means from a first state to a second state when said switching means is operated, a first electrode sensing means coupled to a user at a first point, a second electrode sensing means coupled to the user at a second point, power supply means coupled to supply the electrical energy through said user in a first current path between said first and said second points so as to generate a first electrocardiac signal wherein electrocardiac signals supplied along said input circuit path to said signal processing means are processed by said signal processing means only when said enabling means is in said second state, the improvement comprising: a third electrode sensing means coupled to the user at a third point, a fourth electrode sensing means coupled to the user at a fourth point wherein said power supply means is coupled to supply electrical energy in a second current path to said user between said third and fourth points so as to generate a second electrocardiac signal, control means and interconnecting means selectively coupled between said third and said fourth electrode sensing means and said control means wherein said control means is constructed to prevent said first electrocardiac signal being coupled through said first current path and to allow said second electrocardiac signal to be coupled through said input circuit path to said signal processing means when said interconnection means is coupled to said control means and said enabling means is in its second state and further wherein said first electrocardiac signal is coupled through said input circuit path to said signal processing means when said interconnecting means is not coupled to said control means.

2. In an electrical cardiac monitoring system as claimed in claim 1 a further improvement wherein said control means comprises a first switch means which when actuated couples said power supply means to said first electrode sensor, a second switch means which when actuated couples said second electrode sensor to said input circuit path and a third switch means coupled to said enabling means which is operable only when said interconnecting means is coupled to said control means.

3. In an electrical cardiac monitoring system as claimed in claim 2 a further improvement wherein said interconnecting means comprise a pair of wires each of which is connected to one of said third and fourth electrode sensing means, a resistance connected across said leads, one of said leads being coupled to said power supply means and the other of said leads being coupled to said control means so that when said interconnecting means are connected to said control means a voltage level at a junction point of said control means changes which allows said third switching means to be operable.

4. In an electrical cardiac monitoring system as claimed in claim 2 a further improvement wherein said first electrode sensing means is coupled to said first switch means so that when said first switch means is closed said power supply means is coupled through said first electrode sensing means said enabling means and affects a change in state of said enabling means from its first state to its second state.

5. In an electrocardiac monitoring system as claimed in claim 2 the improvement wherein said first and second switching means are field effect transistors with their drain-source paths coupled in series with said first electrode sensing means and said second electrode sensing means respectively and their gates are coupled together to a junction point of said third switching means which causes said first and second field effect transistors to be conductive when said third switching means is not actuated, and causes said first and second field effect transistor to be operated at a lower conduction level when said third switching means is actuated.

6. In an electrical cardiac monitoring system as claimed in claim 5 the further improvement wherein at least some of said electrode sensing means are constructed of a hydrophilic and conductive polyvinyl chloride which has been treated with an abrasive to remove the glaze and give it a hydrophilic property.

7. In an electrical cardiac monitoring system as claimed in claim 1 the improvement wherein the leads of said interconnecting means are twisted to form a cable which extends at its end to said third electrode sensing means, one lead of said pair of leads is connected to said third electrode sensing means and the other lead of said pair of leads is connected to said fourth electrode sensing means at a point intermediate said third electrode sensing means and said control means.

* * * * *